United States Patent [19]
Ljunggren

[11] Patent Number: 6,003,736
[45] Date of Patent: Dec. 21, 1999

[54] DEVICE FOR CONTROLLED DISPENSING OF A DOSE OF A LIQUID CONTAINED IN A CARTRIDGE

[75] Inventor: Henrik Ljunggren, Ballerup, Denmark

[73] Assignee: Novo Nordisk A/S, Bagsvaerd, Denmark

[21] Appl. No.: 09/088,742

[22] Filed: Jun. 2, 1998

Related U.S. Application Data

[60] Provisional application No. 60/052,977, Jun. 13, 1997.

[30] Foreign Application Priority Data

Jun. 9, 1997 [DK] Denmark .................................. 0675/97

[51] Int. Cl.⁶ .................................................. B65D 88/54
[52] U.S. Cl. ........................... 222/309; 222/333; 222/386; 222/390
[58] Field of Search ..................... 222/309, 333, 222/386, 389

[56] References Cited

U.S. PATENT DOCUMENTS

| | | | |
|---|---|---|---|
| 1,172,820 | 2/1916 | Meegan | 222/309 |
| 3,572,556 | 3/1971 | Pogacar | 222/309 |
| 4,848,606 | 7/1989 | Taguchi et al. | 222/333 |
| 5,219,099 | 6/1993 | Spence et al. | 222/333 |

FOREIGN PATENT DOCUMENTS

| | | | |
|---|---|---|---|
| 2 572 288 | 5/1986 | France . | |
| 3244791 A1 | 7/1984 | Germany . | |
| 3833821 A1 | 4/1990 | Germany . | |
| 0099231 | 4/1991 | Japan | 222/333 |
| WO 96/26754 | 9/1996 | United Kingdom . | |

*Primary Examiner*—Joseph A. Kaufman
*Attorney, Agent, or Firm*—Steve T. Zelson, Esq.

[57] ABSTRACT

The present invention relates to an improved displacement device (1) for controlled dispensing of a dose of a liquid contained in a cartridge (40), the displacement device (1) comprises a housing (5) incorporating: a mechanism (6) for accommodating the cartridge (40), a manually activatable displaceable elongated dose dispensing device (20), the elongated dose dispensing device (20) having a first end part (22) extending to the exterior of the housing (5), an elongated piston rod (30) connected with a displaceable piston (32), the piston (32) being adapted to press out the liquid contained in the cartridge (40), and the piston rod (30) having a plurality of transversely extending teeth (25) arranged along its length, a toothed displacing mechanism (14), and a user-operated dose setting mechanism (8,10,12), the user-operated dose setting mechanism (8,10,12) and the toothed displacing mechanism (14) are operatively connected to cause movement of the toothed displacing mechanism (14) in response to the operation of the dose setting mechanism (8,10,12), pinion mechanism (35) having a shaft (37), being rotatably secured to the elongated dose dispensing device (20), the pinion mechanism (35) being arranged to engage the teeth of the toothed displacing mechanism (14) and the teeth (25) of the piston rod (30).

10 Claims, 1 Drawing Sheet

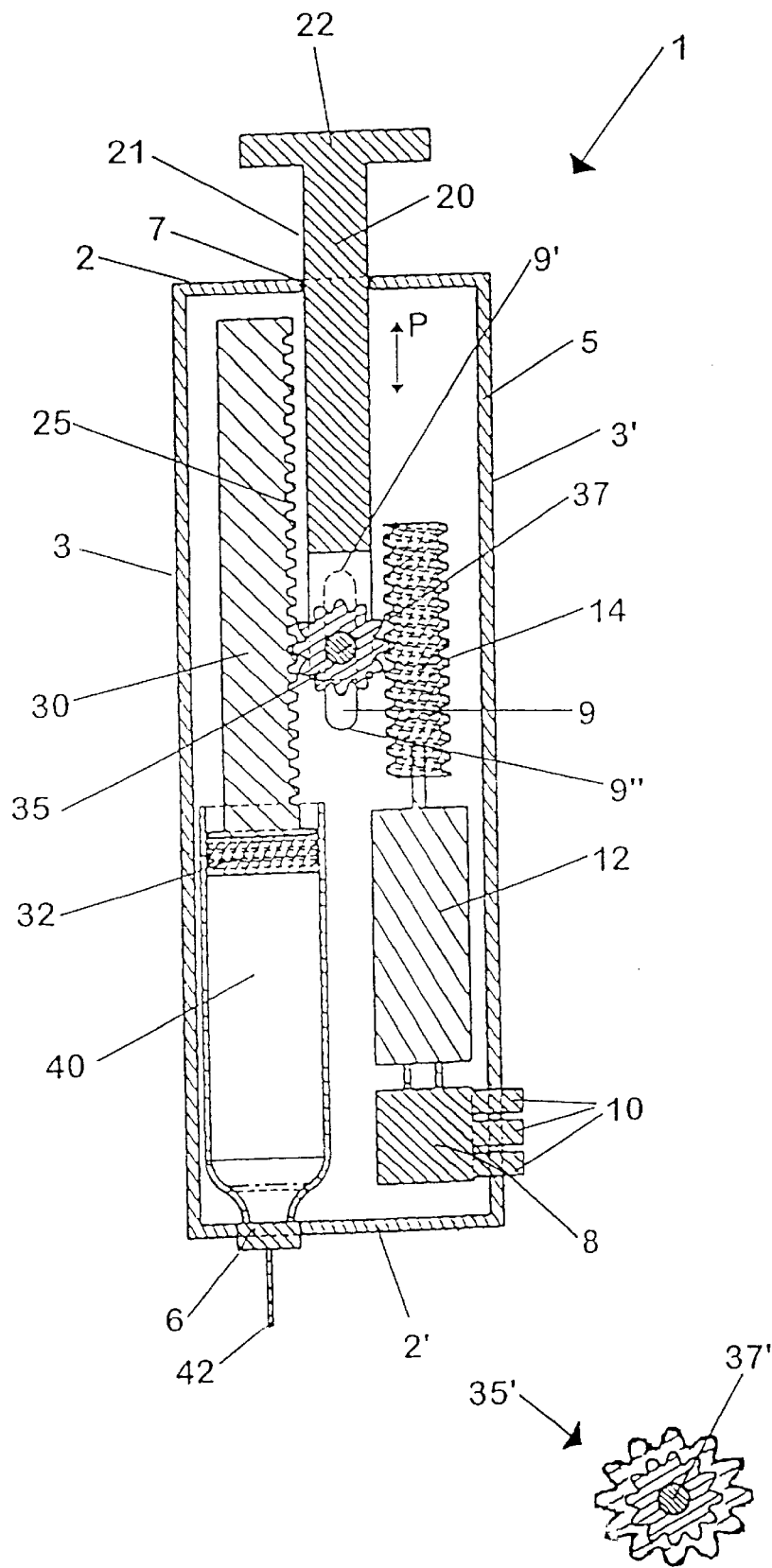

DEVICE FOR CONTROLLED DISPENSING OF A DOSE OF A LIQUID CONTAINED IN A CARTRIDGE

CROSS-REFERENCE TO RELATED APPLICATIONS

This application is a claims priority under 35 U.S.C. 119 of Danish application Ser. No. 0675/97 filed Jun. 9, 1997 and a Provisional application Ser. No. 60/052,977 filed Jun. 13, 1997 the contents of which are fully incorporated herein by reference.

STATEMENT REGARDING FEDERALLY SPONSORED RESEARCH OR DEVELOPMENT

"Not Applicable"

BACKGROUND OF THE INVENTION

The present invention relates to displacement devices for controlled dispensing of a dose of a liquid contained in a cartridge, in particular for use for the infusion of medicine, such as insulin for diabetes patients, and comprising a housing incorporating a means for accommodating said cartridge, a manually activatable displaceable elongated dose dispensing means having a first end part extending to the exterior of the housing, an elongated piston rod connected with a displaceable piston, said piston being adapted to press out the liquid contained in said cartridge.

Such devices are well-known in the art, see eg. FR 2 572 288. Some of the known devices are cumbersome in use, and do not provide means allowing the user to readily verify that a preset dose is in fact dispensed. Other known devices do not permit resetting of the dose when this has been set, rendering the devices impracticable in use.

BRIEF SUMMARY OF THE INVENTION

The invention seeks to provide an improvement of such devices wherein the required dose may be set prior to dispensing, and wherein dispensing is achieved using simple and reliable means. The device according to the invention finds particular use with cartridges containing a dose corresponding to a plurality of consecutive dose setting and dispensing cycles. Using simple means, the device also provides for a clear indication of the actual dose set in that the dose corresponds to the displacement of an elongated dose dispensing means which is subsequently displaced or depressed manually by the user to perform the dispensing. Yet another advantage is that the dose may be set to another value or even reset with a corresponding displacement of the dose dispensing means, without this corresponding displacement leading to dispensing of the liquid. The invention also provides a simple conversion mechanism which may convert a displacement of the dose dispensing means into a displacement of the piston.

The above advantages are achieved by means of a device as indicated in the opening paragraph wherein the elongated piston rod is formed with a plurality of transversely extending teeth arranged along its length, and incorporating a toothed displacing means,
a user-operated dose setting means,
said user-operated dose setting means and said toothed displacing means being operatively connected to cause movement of said toothed displacing means in response to the operation of the dose setting means,
pinion means having a shaft said pinion means being rotatably secured to said elongated dose dispensing means,
said pinion means being arranged to engage the teeth of said toothed displacing means and the teeth of the piston rod.

By adapting the user-operated dose setting means and the toothed displacing means such that the latter is movable upon operation of the dose setting means, the toothed displacing means serves two functions, namely to displace the dose setting means through its movement during the dose setting, and to serve as a fixed toothed rack during dispensing.

According to a preferred embodiment, the toothed displacing means is formed as a screw means having a helical thread, said screw means being caused to rotate about its longitudinal axis in response to the operation of the dose setting means. The screw means provides the advantage that it is a self-blocking member which serves the function of a fixed toothed rack when rotation is stopped.

According to a further embodiment of the invention, the toothed displacing means may be formed as a displaceable, endless toothed rack, means being provided for permitting said toothed rack to be held immovably during dispensing of a dose of liquid.

By forming the piston rod as a flexible member a considerable saving of space may be achieved, leading to a more compact device.

The device may advantageously be provided with at least one guiding surface adapted to control the displacement of the dose dispensing means. Preferably, a guiding surface is adapted to engage the shaft of the pinion means, and may have first and second end surfaces that limit the displacement of the dose dispensing means.

According to a preferred embodiment, the pinion means may be provided with a first and a second set of teeth, the first set of teeth engaging the teeth of the toothed displacing means and the second set of teeth engaging the teeth of the piston rod. In this manner, displacement of the dose dispensing means may be adapted to lead to any desired displacement of the piston.

The user-operated dose setting means may furthermore comprise a motor and a motor control means having a dose selecting means, and the first end part of the displaceable elongated dose dispensing means may be provided with user-inspectable markings indicating the set dose and permitting verification of the setting.

BRIEF DESCRIPTION OF THE DRAWINGS

The invention will now be described in more detail with reference to the drawing which shows a cross-sectional view of a presently preferred embodiment.

DETAILED DESCRIPTION OF THE INVENTION

In the drawing, a device according to the invention for the infusion of a dose of medicine, such as insulin, is generally designated by the reference numeral 1 and comprises a housing 5. In the shown embodiment, the housing 5 is formed with a generally rectangular cross-section and comprises an upper wall 2, a lower wall 2', side walls 3, 3' and end walls, defining a chamber with lodgings for the various components of the device. The housing 5 is preferably shaped so as to allow the device 1 to be held by the hand of a user during the dispensing of liquid medicin from a cartridge 40 accommodated within the housing near the lower wall 2'. The cartridge 40 contains a predetermined amount of medicine corresponding to a number of subsequent infusions, and incorporates a piston 32 at its first or upper end. The frictional engagement of the piston 32 with the cartridge 40 requires a certain minimum pressure to be applied in order to displace the piston 32 and dispense an amount of liquid. A wall portion (not shown) may be removed to give access to the interior of the housing 5 when a new cartridge 40 is to be inserted to replace an empty one. The cartridge is supported at its lower end by a cartridge fixing member 6 arranged at she lower wall 2', allowing a needle 42 to be connected to the cartridge 40 for the purpose of infusion of the medicine.

The device moreover comprises an elongated piston rod 30 which may be formed as a rigid element or as a flexible member as disclosed in WO 95/09021. The piston rod 30 is formed with a plurality of transversely extending teeth 25 or similar elements arranged along its length, the teeth 25 being engageable by a pinion 35, as explained in more detail below. As shown, and when a cartridge 40 is placed within the housing 5, the piston rod 30 is brought to rest against the piston 32 of the cartridge 40.

Shown with the reference numeral 20 is a displaceable elongated dose dispensing means having a first end part 22 extending to the exterior of the housing 5 through an opening 7 which is provided in the top wall 2 and which provides support for the first end part 22 against lateral movement. The dose dispensing means 20 is arranged so as to be displaceable in a direction indicated by the arrow P. The end part 22 provides an upper end surface against which the user of the device may press manually to dispense a preset dose of medicine, and is furthermore provided with a scale on a surface 21 for reasons which will be explained below. At its second or lower end, the dose dispensing means 20 is provided with the abovementioned pinion 35 connected thereto by means of a shaft 37. The displacement of the dose dispensing means 20 is controlled by means of a guiding surface 9 which may be formed as a recess or track arranged in each of the end walls of the housing 5, and which is provided with an upper and a lower surface 9',9" that limit the displacement of the dose dispensing means 20 in any of the directions indicated by the arrow P. The dose dispensing means 20 preferably engages the guiding surface 9 by means of an extension of the shaft 37 of the pinion.

The pinion 35 is arranged to rotate with respect to the dose dispensing means 20, the teeth of the pinion 35 engaging the teeth 25 of the piston rod 30 and also a toothed displacing means 14, which is operatively connected to a user-operated dose setting means 8,10,12 which functions in a manner described below. Consequently, the piston rod 30 and the toothed displacing means 14 provide a support for the lower end of the elongated dose dispensing means 20 against lateral movement.

In the preferred embodiment, the toothed displacing means 14 is formed as a screw means having a helical thread, and is arranged with its longitudinal axis extending perpendicularly to the axis of rotation of the pinion 35. The screw means 14 may be caused to rotate about its longitudinal axis in response to the operation of the dose setting means 8,10,12. As will be apparent, rotation of the screw means 14 will cause rotation of the pinion 35. Due to the frictional engagement of the piston 32 with the cartridge 40, the piston rod 30 remains stationary, causing the dose dispensing means 20 to move in a direction P, depending on the direction of rotation of the screw means 14.

Moreover, in the preferred embodiment, the user-operated dose setting means comprises a motor 12 and a motor control means 8 having dose selecting means 10. The motor 12 has an output shaft connected to the toothed displacing means 14, causing the latter to rotate as indicated above.

In operation, the user selects a desired dose of medicine to be dispensed by providing this information to the motor control means 8 via the dose selecting means 10. In the zero-setting, the shaft 37 of the pinion 35 rests against the lower surface 9" of the guiding surface 9. When the dispensing procedure is to be initiated, the motor 12 is activated, causing rotation of the displacing means 14 corresponding to the selected dose. This rotation is converted into an upward displacement of the dose dispensing means 20, causing its upper end surface to rise above the upper wall 2 of the housing 5, thereby making the scale on the surface 21 visible. The displacement of the dose dispensing means 20 will depend on the chosen gear ratio, and the setting of the dose selecting means 10 may be verified by inspecting the scale on the surface 21 which is graduated in accordance with the chosen gear ratio.

When the dose dispensing means 20 has been displaced in accordance with the desired dose, the motor 12 automatically stops and the device is ready for dispensing the desired amount of medicine. If the user wishes to change the dose, eg. upon inspection of the scale, the motor control means 8 may be caused to reset the device through rotation of the screw means 14 in a given direction, leading to a corresponding further displacement of the dose dispensing means 20.

When dispensing is eventually desired, the displacing means 14 is blocked against movement so as to perform the operation of a fixed toothed rack and the needle 42 is inserted into the body of the user. By using a self-blocking screw means having a helical thread, this situation is automatically reached when the motor 12 is stopped. Where the displacing means 14 is alternatively provided by eg. a motor-driven displaceable rack, it may be necessary to provide engagement means to lock the rack against displacement. When a downward pressure is subsequently applied by the user to the end part 22 of the dose dispensing means 20, the pinion 35 will rotate and move downward along the blocked displacing means 14 until the shaft 37 reaches the lower surface 9" of the guiding surface 9. This movement is converted into a simultaneous downward displacement of the piston rod 30 and the piston 32, whereby the desired amount of liquid is dispensed. It may be noted that the "active" part of the piston rod 30, ie. the teeth 25 that are engaged by the pinion 35 during dose setting and dispensing, shifts from an area close to the piston 32 when the cartridge 40 is full, to an area of the piston rod 30 close to its free end when the cartridge 40 is empty.

When a cartridge is to be replaced by another, the teeth 25 of the piston rod 30 may be disengaged from the pinion means 35, allowing the piston rod 30 to be shifted to the position shown on the drawing whereby extraction of the empty cartridge is made possible. Alternatively, the dose dispensing means 20 may be pushed into the housing such that the shaft 37 rests against the lower end surface 9" and restricts further downward movement of the dose dispensing means 20, and the displacing means 14 be operated in a reversed manner, whereby the piston rod 30 is shifted. The piston rod 30 is subsequently brought to rest against the piston of a new cartridge inserted into the housing 5, the teeth 25 of the piston rod 30 engaging with the pinion 35.

It should be noted that the upper end surface 9' of the guiding surface 9 provides a safeguard against inadvertent setting of a dose exceeding a maximum permitted dose.

When the shaft 37 reaches the limit 9' of the guiding surface 9, further rotation of the screw means 14 will lead to immediate dispensing of liquid prior to the instant when the needle 42 is inserted into the body of the user, thus providing a visible warning. By varying the distance between the end surfaces 9', 9" the device may be adapted for different maximum permitted doses.

In the drawing, a pinion 35 with only one set of teeth is shown. An alternative pinion 35' is shown in the lower part of the drawing, and is provided with a second set of teeth fixed to the shaft 37' at a distance from the first set of teeth, said first set of teeth engaging the teeth of the toothed displacing means 14, said second set of teeth engaging the teeth 25 of the piston rod 30. In this manner, a gearing may be achieved, whereby displacement of the dose dispensing means 20 leads to a desired displacement of the piston 32 other than the 1:2 ratio achieved with the arrangement shown in the top part of the drawing, eg. a 2:1 or a 1:1 gearing.

Although the user-operated dose setting means has been described and illustrated as comprising a motor unit 12, it should be noted that this unit may be replaced by any manually driven means that provide for a movement of the toothed displacing means in accordance with a desired dose. Also, the cartridge may be provided with a piston integrally connected with a piston rod, in which case a new piston rod is employed whenever the cartridge is replaced.

I claim:

1. A displacement device (1) for controlled dispensing of a dose of a liquid contained in a cartridge (40), said displacement device (1) comprising a housing (5) incorporating:
   a means (6) for accommodating said cartridge (40),
   a manually activatable displaceable elongated dose dispensing means (20),
      said elongated dose dispensing means (20) having a first end part (22) extending to the exterior of the housing (5),
   an elongated piston rod (30) connected with a displaceable piston (32),
      said piston (32) being adapted to press out the liquid contained in said cartridge (40), and
      said elongated piston rod (30) having a plurality of transversely extending teeth (25) arranged along its length,
   a toothed displacing means (14),
   a user-operated dose setting means (8,10,12),
      said user-operated dose setting means (8,10,12) and said toothed displacing means (14) being operatively connected to cause movement of said toothed displacing means (14) in response to the operation of the dose setting means (8,10,12),
   pinion means (35) having a shaft (37),
      said pinion means (35) being rotatably secured to said elongated dose dispensing means (20),
   said pinion means (35) being arranged to engage the teeth of said toothed displacing means (14) and the teeth (25) of the piston rod (30).

2. A displacement device according to claim 1, characterized in that
   the toothed displacing means (14) is formed as a screw means having a helical thread, said screw means being caused to rotate about its longitudinal axis in response to the operation of the dose setting means (8,10,12).

3. A displacement device according to claim 1, characterized in that
   the toothed displacing means (14) is formed as a displaceable endless toothed rack, means being provided for permitting said toothed rack to be held immovably during dispensing of a dose of liquid.

4. A displacement device according to claim 1, characterized in that
   the piston rod (30) is formed as a flexible member.

5. A displacement device according to claim 1, characterized in that
   said housing (5) comprises guiding surfaces (7,9) for supporting the dose dispensing means (20), one of said guiding surfaces being preferably formed by an opening (7) in said housing and engaging said first end part (22) of the elongated dose dispensing means (20).

6. A displacement device according to claim 5, characterized in that
   said housing (5) comprises a guiding surface (9,9',9") adapted to control the displacement of said dose dispensing means (20).

7. A displacement device according to claim 6, characterized in that
   said guiding surface (9,9',9") engages said shaft (37) of the pinion means (35),
   said guiding surface (9.9',9") is formed by an elongated track extending in parallel with the elongated dose dispensing means (20), and has first and second end surfaces (9',9") adapted to limit the displacement of said dose dispensing means (20).

8. A displacement device according to claim 1, characterized in that
   said pinion means (35) is provided with a first and a second set of teeth, the first set of teeth engaging the teeth of said toothed displacing means (14) and the second set of teeth engaging the teeth (25) of the piston rod (30).

9. A displacement device according to claim 1, characterized in that
   said user-operated dose setting means comprises a motor (12) and a motor control means (8) having a dose selecting means (10).

10. A displacement device according to claim 1, characterized in that
    said first end part (22) of said displaceable elongated dose dispensing means (20) is provided with user-inspectable markings (21) indicating the set dose.

* * * * *

UNITED STATES PATENT AND TRADEMARK OFFICE
CERTIFICATE OF CORRECTION

PATENT NO.       : 6,003,736
DATED            : December 21, 1999
INVENTOR(S)      : Henrik Ljunggren It is certified that error appears in the above-identified patent and that said Letters Patent is hereby corrected as shown below:

Title page,
ABSTRACT,
Line 11, please delete "and the piston", and insert -- and the elongated piston --.
Line 20, please delete "being", and insert -- are --.

Signed and Sealed this

Twenty-sixth Day of February, 2002

Attest:

JAMES E. ROGAN
*Attesting Officer*          *Director of the United States Patent and Trademark Office*